United States Patent [19]

Bengtsson et al.

[11] 4,334,110
[45] Jun. 8, 1982

[54] METHOD OF PRODUCING SYMMETRICAL TRINITROBENZENE

[75] Inventors: Erik Bengtsson; Nils Billingsson, both of Karlskoga; Karl-Johan Persson, Storfors; Bengt-Olov Bäckman, Karlskoga, all of Sweden

[73] Assignee: Aktiebolaget Bofors, Bofors, Sweden

[21] Appl. No.: 190,136

[22] Filed: Sep. 24, 1980

[30] Foreign Application Priority Data

Sep. 27, 1979 [SE] Sweden ............................... 7908005

[51] Int. Cl.$^3$ ....................... C07C 76/02; C07C 79/10
[52] U.S. Cl. ................................................. 568/932
[58] Field of Search ........................ 568/932, 933, 934

[56] References Cited

U.S. PATENT DOCUMENTS

| | | | |
|---|---|---|---|
| 2,858,346 | 10/1958 | Diels et al. | 568/932 |
| 2,874,196 | 2/1959 | Norell | 568/932 |
| 3,507,924 | 4/1970 | Hakansson et al. | 568/932 |
| 4,261,908 | 4/1981 | Schroeder et al. | 568/931 |

FOREIGN PATENT DOCUMENTS 77353 11/1893 Fed. Rep. of Germany ...... 568/932

OTHER PUBLICATIONS

Claus, A., et al., Ber. d. d. Chem. Gesellschaft, vol. 16, pp. 1596–1598 (1883).

Primary Examiner—Teddy S. Gron
Attorney, Agent, or Firm—Pollock, Vande Sande & Priddy

[57] ABSTRACT 1,3,5-trinitrobenzene is produced through direct oxidation of 2,4,6-trinitrotoluene with nitric acid.

9 Claims, No Drawings

METHOD OF PRODUCING SYMMETRICAL TRINITROBENZENE

The present invention relates to a method of producing 1,3,5-trinitrobenzene (symmetrical trinitrobenzene or symmetrical TNB) through direct oxidation from 2,4,6-trinitrotoluene, trotyl (TNT), or mixtures of 2,4,6-trinitroluene with other nitrotoluenes.

1,3,5-trinitrobenzene (symmetrical TNB) is of commercial interest as a raw material for the production of phloroglucin (1,3,5-trihydroxy benzene) and its derivatives and as an explosive. Hitherto, the compound has been produced through oxidation of 2,4,6-trinotrotoluene (TNT) with bichromate and sulphuric acid, and as an intermediary, trinitrobenzoic acid has then been obtained. This method gives a poor yield, and does not utilize the reaction apparatus well, and the method therefore leads to a high price of the product obtained, the quality of which will moreover be poor. Further, the method is full of risks, and very unsuitable from an environmental point of view, as poisonous chromium salts are obtained as residual products.

According to the present invention, it has now surprisingly been found that 2,4,6-trinitrotoluene (TNT) can be oxidized with nitric acid in one step directly to 1,3,5-trinitrobenzene (symmetrical TNB). It has also proved possible, in a corresponding way, to oxidize by-products from the manufacture of trinitrotoluene (TNT), so-called tri oil, to pure trinitrobenzene (TNB) in spite of the fact that the tri oil contains large quantities of impurities. It has thus surprisingly proved possible to decompose these impurities, under oxidation, to low-molecular compounds, whereby pure trinitrobenzene (TNB) can be isolated from the final product obtained. According to the method characteristic for the invention, mixtures of trinitrotoluene (TNT) and the impurities obtained at the manufacture of trinitrotoluene (TNT) can also be oxidized. This can be done by the spent acids from the crystallization of pure trinitrotoluene (TNT) being directly subjected to oxidation. In this way, environmental and safety problems can be solved, and a valuable product produced from the waste product which would otherwise have to be destroyed, at considerable costs.

According to the present invention, the oxidation of trinitrotoluene and/or by-products from the manufacture of trinitrotoluene must be carried out at a high temperature and under pressure. This is a dangerous process, and a special technique is required if it is to be carried out without explosions. Within the scope of the invention, we have developed such a technique, which involves a remote-controlled, continuous process.

According to this technique, the trinitrotoluene is oxidized with nitric acid in a tubular, vertical reactor which, quite generally, consists of a vertical tube, into the lower part of which the components which are to be reacted with each other are fed, in this case nitric acid and trinitrotoluene or, alternatively, tri oil. The stirring in the reactor tube is achieved by the gases which are formed during the reaction, while the pressure in the reactor is adjusted by changing the flow speed of the reaction mixture. The ratio of the length to diameter of the reactor can be between about 100:1 and 100:2, or in the vicinity of this. There are many advantages of having a rapid reactor of the above-mentioned kind. For instance, the quantity of high-explosive mixture in the actual reactor will be small at all times, and it is easy to arrange to have the reactor screened of, and protection arranged for the personnel and the sensitive apparatus required for supervision of the reactor.

The invention has been defined in the following claims, and will now be further described in connection with some examples.

EXAMPLE 1

Ampoule Tests

For the ampoule tests, glass ampoules were utilized, each containing 4 cm$^3$. With a wall thickness of 1.3 mm, these ampoules withstood a pressure of at least 70 atmospheres. For the stirring, a vibrator was used, which entirely emulsified the trinitrotoluene and the acid phase (nitric acid) with each other. The heating took place by having the ampoule entirely immersed in an oil bath. The temperature was measured with thermocouples in the oil bath. At all of these tests, the volumetric efficiency was approx. 10%.

When the ampoules had been filled with 2,4,6-trinitrotoluene (TNT) and nitric acid (HNO$_3$) and sealed, they were vibrated for a predetermined number of minutes in the oil bath, which had been set at the temperature intended. They were thereafter removed from the bath and allowed to self-cool, after which they were crushed, and the contents extracted with warm chloroform. The chloroform solution was washed with a diluted sodium carbonate solution and water, and totally evaporated. The residue was weighed, and its melting point was determined.

The excess of nitric acid at the ampoule tests was 100% of the theoretical quantity, which is two moles of nitric acid per mole of 2,4,6-trinitrotoluene.

Very good results were obtained at oxidation with 65% nitric acid. At such a test, in which 0.162 g 2,4,6-trinitrotoluene was oxidized, and at which the temperature was 220° C. and the reaction time 5 minutes, a product was obtained with a melting point of 121.5°–123.5° C. with a yield of 87%. According to the literature, the melting point of 1,3,5-trinitrobenzene should be 122° C.

A lower concentration of acid than 65% gave a lower yield, and sometimes a lower melting point.

EXAMPLE 2

Autoclave Tests

For these tests, a 280 ml high-pressure autoclave of titanium provided with a magnetic stirrer was used. An oil bath was used for the heating. The temperature was measured with thermocouples in the bath and in the autoclave (thermometer pocket). The pressure was measured with a manometer fastened in the cover of the autoclave.

When 2,4,6-trinitroluene and nitric acid HNO$_3$ had been charged, heating took place as rapidly as possible until the reaction started, which as a rule took place between 180° and 190° C. The fact that the reaction had started was primarily noticed by the increase in pressure in the autoclave. As soon as the reaction had started, the heating was reduced to one-half effect. In order to maintain the reaction temperature desired, and so that the pressure should not exceed approx. 40 atmospheres, part of the gases formed had to be let out via a valve in the cover of the autoclave. Shortly after gas no longer needed to be let out, the oxidation was considered to be complete, and the autoclave with contents was cooled to room temperature. The contents were thereafter processed as in example 1.

While a 100% excess of nitric acid was sufficient for the ampoule tests, at least a 350% excess was required at the autoclave tests, in order that a satisfactory result should be obtained as regards the melting point and colour of the product. One of the reasons for this is in all probability that the pressure must certainly have been higher at the ampoule tests.

Also at the autoclave tests, better results were obtained with 65% nitric acid than with lower concentrations. However, the yield was lower than at the ampoule tests, although still very satisfactory with consideration to the high-nitrated compound (explosive) which was to be oxidized. As an example may be mentioned a test at which 48 g 2,4,5-trinitrotoluene was oxidized, and in which the excess of nitric acid was 350%, the reaction temperature max. 212° C., and the reaction time about 20 minutes. In this case the yield was 63% and the melting point 118.5°–120° C. With a still higher excess than in this test, the yield increased somewhat.

EXAMPLE 3

In this case, the oxidation of 2,4,6-trinitrotoluene was carried out in a 2.8 l high-pressure autoclave, which was provided with an electric heating jacket and stirrer with motor, and a valve for controlling the pressure through evacuation of gases. Both the temperature and the pressure were measured continuously, with recorders.

At each test in this autocalve, 500 g 2,4,6-trinitrotoluene was oxidized with 65% nitric acid in a 350% excess. There were certain differences in max. temperature (215°–223° C.), max. pressure (35–44 atmospheres) and reaction time (20–25 min.) between these tests.

After the reaction had been completed, the charge was pressed over into a closed vessel containing water, where the contents were cooled to room temperature before filtering off the raw product, which was washed with water and dried.

In order to raise the melting point, the raw product was dissolved in acetone and precipitated through addition of water.

The mean yield from 5 tests was about 60% reprecipitated product, counted on the theoretical quantity of charged 2,4,6-trinitrotoluene.

EXAMPLE 4

Oxidation of Tri Oil

So-called tri oil is obtained by the mother liquor (raw acid) from the recrystallization of raw TNT being evaporated in nitric acid. The main component in the tri oil is various trinitrotoluene isomers and 2,4-dinitrotoluene. About one-half of the tri oil consists of 2,4,6-trinitrotoluene. In the same autoclave as the one used for example 2, a number of oxidations of tri oil with nitric acid of varying concentrations and excesses were carried out. As unsymmetrical trinitrotoluene and 2,4-dinitrotoluene can easily be decomposed, and gas formation was greater than at the oxidation of only symmetrical trinitrotoluene. The pressure was therefore allowed to rise more at the oxidation of tri oil, sometimes up towards 100 atmospheres. The highest reaction temperature was 228° C.

When the reaction seemed to have been completed, in general, judging from the pressure changes in the autoclave, the oxidation charge was cooled to room temperature and filtered. The raw product then obtained was leached in a 10% sodium bicarbonate solution, to remove the small quantities of acid impurities, primarily 2,4-dinitrobenzoic acid, which it contained.

The best result was obtained at oxidation with 65% nitric acid in an excess of 350% or more, counted on all the nitro compounds included in the tri oil. The yield was approx. 70% counted on the 2,4,6-trinitrotoluene included in the tri oil, and the melting point was 122°–124° C.

EXAMPLE 5

In this example it is shown that so-called raw acid from recrystallization of raw TNT can be used for the production of 1,3,5-trinitrobenzene (TNB) without first having been evaporated to tri oil.

Before the oxidation, the concentration of nitric acid was increased from approx. 50% to 65% through the addition of fuming 99% nitric acid. The quantity of nitric acid then became so great in relation to the 2,4,6-trinitrotoluene plus other nitro compounds included in the raw acid that a certain extra quantity of trinitrotoluene could be added for oxidation together with the contents of the raw acid.

The oxidations were carried out in the same autoclave as the one used in examples 2 and 4. The pressure was allowed to rise more than at the oxidation of only 2,4,6-trinitrotoluene, although not as high as at the oxidation of tri oil.

In such a test, a mixture of 153 g raw acid (containing 9.8 g nitrotoluenes, of which 4.7 g was 2,4,6-trinitrotoluene), 55.6 g 99% nitric acid, and 44.5 g TNT was oxidized. The composition involves that the nitric acid is 65% and in an excess of approx. 400%. The highest reaction temperature was 224° C. For the recovery, the contents of the autoclave were allowed to cool to 60° C., after which the precipitation was filtered off, washed with water, and dried. A yield of 69% as obtained, counted on the total quantity of 2,4,6-trinitrotoluene.

EXAMPLE 6

The oxidation was carried out in a vertically placed tubular reactor, and the nitric acid ($HNO_3$) TNT (2,4,6-trinitrotoluene) and the raw acid were pumped into the bottom of the reactor, and the reaction products were taken out from the upper part of the reactor. The acid concentration was 60%, and the excess of acid 300%. The temperature was varied at various tests between 200° and 240° C. The yield was of the same order as for example 5.

We claim:

1. A method of producing 1,3,5-trinitrobenzene (symmetrical trinitrobenzene) through direct oxidation of 2,4,6-trinitrotoluene (TNT) with nitric acid ($HNO_3$) under pressure and at an elevated temperature above 150° C. wherein said oxidation is carried out as a continuous process by feeding 2,4,6-trinitrotoluene and a theoretical excess of nitric acid of at least 100% based on the 2,4,6-trinitrotoluene into the lower part of a vertical reaction zone containing a vertical tube with a length to diameter ratio of 100:1 to 100:2, causing the reactants to flow through said vertical reaction zone under continuous stirring achieved by gases formed during the reaction between the reactants, maintaining the pressure in said reaction zone about 15 kg/cm² by adjusting the flow speed of the reactants and product through said reaction zone; and removing reaction product from the upper part of said reaction zone.

2. The method of claim 1 wherein the reaction temperature is 190°–240° C.

3. The method of claim 1 or 2 wherein said theoretical excess of nitric acid is at least 200%.

4. The method of claim 1 or 2 wherein said nitric acid charged has a concentration of at least 60%.

5. The method of claim 1 or 2 wherein said nitric acid charged has a concentration of 60–65%.

6. The method of claim 1 or 2 wherein the 2,4,6-trinitrotoluene starting material is substantially pure 2,4,6-trinitrotoluene.

7. The method of claim 1 or 2 wherein the 2,4,6-trinitrotoluene starting material is tri oil from the recrystallization of raw 2,4,6-trinitrotoluene.

8. The method of claim 1 or 2 wherein the 2,4,6-trinitrotoluene starting material is a mixture of raw acid from the recrystallization of raw 2,4,6-trinitrotoluene and substantially pure 2,4,6-trinitrotoluene.

9. The method of claim 1 or 2 wherein the 2,4,6-trinitrotoluene starting material is raw acid (mother liquor) from the recrystallization of raw 2,4,6-trinitrotoluene.

* * * * *